United States Patent [19]

Yost et al.

[11] Patent Number: 4,954,452
[45] Date of Patent: Sep. 4, 1990

[54] NON-METAL COLLOIDAL PARTICLE IMMUNOASSAY

[75] Inventors: David A. Yost, Round Lake Park, Ill.; John C. Russell, Greenfield, Wis.; Heechung Yang, Green Oaks, Ill.

[73] Assignee: Abbott Laboratories, Abbott Park, Ill.

[21] Appl. No.: 72,084

[22] Filed: Jul. 9, 1987

[51] Int. Cl.$^5$ .............. G01N 33/551; G01N 33/566; G01N 33/543; G01N 33/536

[52] U.S. Cl. ................................. 436/524; 436/501; 436/518; 436/523; 436/536; 436/541; 436/544; 436/800; 436/808; 436/824; 436/825

[58] Field of Search .............. 436/501, 518, 523, 528, 436/536, 541, 544, 800, 824, 825, 808, 524

[56] References Cited

U.S. PATENT DOCUMENTS

| | | | |
|---|---|---|---|
| 4,022,876 | 5/1977 | Anbar | 424/1 |
| 4,122,030 | 10/1978 | Smith et al. | 430/84 X |
| 4,313,734 | 2/1982 | Leuvering | 23/230 B |
| 4,341,757 | 7/1982 | Spallholz | 424/8 |
| 4,373,932 | 2/1983 | Gribnau et al. | 436/501 |

Primary Examiner—Robert J. Warden
Assistant Examiner—Jack Spiegel
Attorney, Agent, or Firm—Daniel R. Curry

[57] ABSTRACT

A method of performing a diagnostic immunoassay utilizing colloidal non-metal particles having conjugated thereto a binding component capable of specifically recognizing an analyte to be determined. After reaction of the sample and colloidal non-metal particles, the presence or amount of analyte/colloidal non-metal particle complexes are determined by optical analysis as a measure of the amount of analyte in the sample. The method can be utilized for the specific detection of numerous analytes and is sensitive and has a wide detection range.

28 Claims, 2 Drawing Sheets

NON-METAL COLLOIDAL PARTICLE IMMUNOASSAY

BACKGROUND OF THE INVENTION

The present invention relates generally to diagnostic immunoassays and material useful therein More particularly, the present invention relates to employing colloidal non-metal particles, especially selenium in specific binding assays to determine the presence of small quantities of an analyte of interest Various analytical procedures are commonly employed in assays to determine the presence and/or concentration of substances of interest or clinical significance in fluids or other materials. Such clinical significant or interesting substances are commonly termed "analytes" and can include, for example, antibodies, antigens, and the broad category of substances commonly known by the term "ligands". Particularly, with respect to the diagnosis and treatment of disease or other conditions of the human body, the accurate determination, on a timely basis, of the presence or amount of certain analytes can have a profound influence on the ability of health care professionals to treat and manage pathological physical disorders or make an early and accurate determination of physiological conditions such as pregnancy.

Many diagnostic immunoassays are known which generally employ the specific binding characteristics that exist between an analyte or protein and a specific antibody tagged with some traceable substituent. Assays of these type include, for example, radioimmunoassay (RIA), free radical assay technique (FRAT), enzyme immunoassay technique (EIA), and immunofluorescence techniques such as fluorometric analysis and fluorescence polarization. Analytes of interest have also been detected and/or quantified using metal sol particle immunoassay techniques, as described in U.S. Pat. No. 4,313,734 to Leurverinq. In Leurverinq, colloidal metal particles of at least 5 nm are coupled to binding protein and employed as an aqueous sol dispersion in immunochemical techniques such as "sandwich" assays and homogeneous agglutination assays.

While the above techniques can be effective, they are subject to improvement. For example, although sensitive, a radioimmunoassay requires handling of radioactive compounds and use of sensitive instrumentation, such as a scintillation counter. Enzyme immunoassays are widely used; however, in general EIA's are not sensitive enough to detect small amounts of immunogens. Immunoassays employing metal sols are subject to limited detection range (i.e, wavelenqth range to monitor reaction) thereby requiring careful calibration of the instrument employed to monitor the change in optical properties of a sample.

Accordingly, there is a need for an improved method for conducting an immunoassay exhibitinq both high sensitivity and a wide detection range for analytes and proteins of interest.

SUMMARY OF THE INVENTION

The present invention relates to a non-metal colloidal particle suitable for use in an immunoassay. The method of the present invention involves determining the presence or amount of an analyte in a sample by, contacting the sample with a non-metal labelled constituent comprising an aqueous dispersion of colloidal non-metal particles having conjuqated thereto a binding component capable of specifically recognizing the analyte of interest. After reaction of the sample and non-metal labelled constituent the presence or amount of analyte/colloidal non-metal particle complexes formed are analyzed as a measure of the amount of analyte in the sample.

In a preferred embodiment of the present invention, selenium particles having an antibody adsorbed thereon serve as the non-metal labelled constituent. Preferably, selenium particles of from about 3 nm to about 450 nm are used, with selenium particles of from about 11 nm to about 200 nm most preferred. The selenium particles are employed in the preferred method as an aqueous dispersion of from about 0.005% to about 0.1% (weight/volume). Most preferably, an aqueous dispersion of from about 0.02% to about 0.04% (weight/volume) selenium particles is used.

The method of the present invention is suitable for solution type immunoassays and chromatographic assays employing solid carriers such as nitrocellulose or the like. In a preferred embodiment, the presence or amount of analyte is determined by measuring the change in optical properties in a reaction mixture of test sample and aqueous dispersion of colloidal non-metal labelled constituent resulting from agglutination of analyte and colloidal non-metal labelled constituent. While the change of optical properties can be detected either visually or by use of instrumentation, preferably the change in optical properties is analyzed using a spectrophotometer or fluorescence intensity measuring instrument.

DETAILED DESCRIPTION OF THE INVENTION

Figure 1:
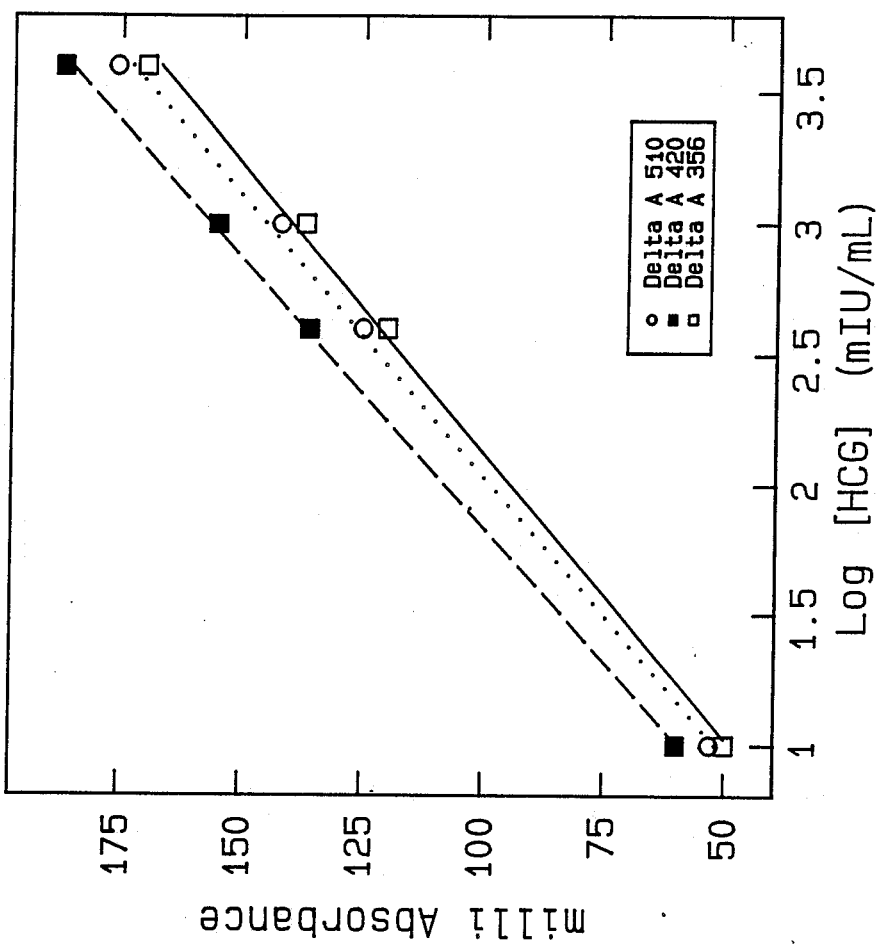
FIG. 1 is a graphic representation of optical density measurements at various wavelengths for hCG samples analyzed using the method of the present invention.

The term "analyte" as used herein is defined as a compound or composition to be measured, which may be an antibody, antigen or ligand, which is mono- or polyepitopic, antigenic or haptenic, single or plurality of compounds which share at least one common epitopic site or a receptor. Ligand, as used herein, refers to a molecule, to which a binding protein, such as a receptor or an antibody, can be obtained or formed. Liqands are generally protein-free compounds, generally of low molecular weight, which do not induce antibody formation when injected into an animal but which are reactive to antibodies. Liqands which are chemically modified for configuration to a carrier material, such as a protein or tracer compound are termed haptens. Antibodies to haptens are generally raised by first conjugatinq the haptens to a protein and injecting the conjugate product into an animal. The resulting antibodies are isolated by conventional antibody isolation techniques.

Generally, in the present invention, the immunological reaction is based on the reaction between a specific binding protein (i.e. antigen or antibody) and the analyte which is a corresponding bindable substance in an aqueous test sample. In the present invention, the analyte of interest in the test sample can be any one of a large number of antigens, antibodies, or ligands of interest. The corresponding binding protein is an antigen or antibody capable of specifically recognizing the corresponding analyte.

The analytes to be determined using the method of the present invention are limited primarily by their ability to be attached to the specific binding component. Generally, the molecular weight will be between 100 and about 100,000; however, the present method can be applied to detect macro-molecules of a much higher molecular weight. Antigens, haptens and their antibodies, hormones, vitamins, drugs, metabolites and their receptors and binding materials may be determined using the present method. Representatives of analytes determinable by the method of the present invention include steroids such as estrone, estradiol, cortisol, testosterone, progesterone, chenodeoxycholic acid, digoxin, cholic acid, digitoxin, deoxycholic acid, lithocholic acids and the ester and amide derivatives thereof; vitamins such as B-12, folic acid, thyroxine, triiodothyronine, histamine, serotorin, prostaqlandins such as PGE, PGF, PGA; antiasthmatic drugs such as theophylline, antineoplastic drugs such as doxorubicin and methotrexate; antiarrhythmic drugs such as disopyramide, lidocaine, procainamide, propranolol, quinidine, N-acetylprocainamide; anticonvulsant drugs such as phenobarbital, phenytoin, primidone, valproic acid, carbamazepine and ethosuximide; antibiotics such as penicillins, cephalosporins, erythromycin, vancomycin, gentamicin, amikacin, chloramphenicol, streptomycin and tobramycin; antiarthritic drugs such as salicylate; antidepressant drugs including tricyclics such as nortriptyline, amitriptyline, imipramine and desipramine; and the like as well as the metabolites thereof.

Additional liqands that may be determined by the methods of the present invention include drugs of abuse such as morphine, heroin, hydromophone, oxymorphone, metapon, codeine, hydrocodone, dihydrocodiene, dihydrohydroxy codeinone, pholcodine, dextromethorphan, phenazocine and deonin and their metabolites. Higher molecular weight analytes such as aminoacids, polypeptides, and proteins such as hCG, TSH, LH, ferritin, CEA and C-reactive protein may also be determined by the methods of the present invention.

According to the present invention a method for performing immunoassays employing a non-metal labelled constituent in the form of a aqueous dispersion of colloidal non-metal particles having conjuqated thereto a specific binding component (i.e. antibody or antigen) has been found to be surprisingly useful. Preferred non-metals which can be used in the present invention include elements within Group VI A. of the Periodic Table, sulfur, selenium, and tellurium. Most preferably the present invention utilizes an aqueous dispersion of colloidal selenium particles.

The aqueous dispersion of colloidal non-metal particles can include from about 0.005g to about 0.1g, on a weight/volume basis, of the colloidal non-metal particles. Most preferably, aqueous dispersions having from about 0.02% to about 0.04% of the non-metal particles on a weight/volume basis are used. The non-metal particles themselves preferably have a particle size from about 3 nm to about 450 nm, most preferably from about 11 nm to about 200 nm. In the case of the most preferred selenium particles the overall shape is globular and exhibits a ratio of length to width of between 0.7 and 0.95. Surprisingly, as evidenced by the examples hereto it has been observed that use of colloidal non-metal particles conjugated to a binding protein provides for an immunoassay exhibiting high sensitivity and wide detection range for an analyte of interest.

While the immunocomponent of the non-metal labelled constituent can be conjugated to the colloidal non-metal particles using a number of methods known in the art including physical immobilization, covalent bonding hydrophilic bonding, hydrophobic bonding and ionic interaction preferably antibody capable of specifically recognizing the analyte of interest is adsorbed onto the colloidal non-metal particles.

The method of the present invention involves contacting a liquid sample, having or suspected of having an analyte of interest, with a labelled substance and binding component capable of recognizing the analyte sought to be quantified. In a preferred embodiment, a sample of biological fluid such as urine, blood, serum, saliva or the like is mixed with an aqueous dispersion of non-metal labelled constituent in the form of colloidal selenium particles having conjugated thereto a binding compound capable of recognizing the analyte of interest. After an appropriate incubation time, (i.e. sufficient time to allow the labeling substance to complex with all the analyte of interest in the sample) the presence or amount of analyte/selenium labelled constituent complexes is determined as a measure of the amount of analyte in the sample. In the preferred embodiment the change in optical properties resulting from formation of the analyte/colloidal selenium labelled constituent complexes is measured.

The measurement of the change in optical properties can be performed using a number of known techniques. The particular manner in which the change in optical properties is determined depends on the immunoassay techniques employed. For example, the present method can be used in liquid chemistry immunoassay techniques such as homogeneous agglutination in which the immunoloqical component of interest in the test sample complexes with the labelled immunochemical component resulting in a change of optical properties. Also, the present method can be employed in solid carrier type immunoassays which involve "sandwich" techniques known to those skilled in the art. The typical sandwich assay of this type includes an immunological component, such as a non-metal labelled antibody, if an antigen is to be determined, rendered insoluble by coupling to the solid carrier such as the surface of a reaction vessel or fiber matrix. After an initial incubation period which can be followed by a washing step, a second incubation takes place with a reagent capable of participating in a specific binding reaction with the analyte/non-metal labelled antibody complex formed during the initial incubation period.

In the case of homoqeneous liquid agglutination techniques employing the method of the present invention, optical changes can be detected in a number of known ways. In one preferred method the change in optical properties resulting from formation of analyte/colloidal non-metal labelled constituent complexes are measured using a visual spectrophotometer, such as the ABBOTT SPECTRUM® available from Abbott Laboratories, Abbott Park, Ill. 60064. Alternatively, known fluorescence quenching techniques can be employed to determine the change in optical properties based on the fluorescence intensity of analyte/colloidal non-metal labelled complexes formed in the reaction mixture. Fluorescence intensity can be detected and/or quantified using commercially available clinical instruments such as the Abbott TDx ®, available from Abbott Laboratories, Abbott Park, Ill. 60064.

It is contemplated that the method of the present invention can be employed not only in the above-described immunoassay techniques but can be modified by one of skill in the art for carrying out numerous heteroqeneous and, homogeneous specific binding assays without departing from the inventive concepts embodied herein. For example the method of the present invention can be modified to employed non-metal labelled constituent in nephelometry or histochemistry.

When the method of the present invention is employed using colloidal selenium particles immunoassays with sensitivity detection as low as 10 mIU/ml and at least up to 5,000 mIU/ml can be conducted. Further, not only does use of colloidal selenium having binding component conjugated thereto make possible high detection sensitivity when employed in the present method, but, the wavelength range for accurately detecting and quantifying an immunoreactive response is surprisingly wide. For example as presented in the Examples hereto, formation of analyte/colloidal selenium binding component complexes may be accurately measured over the range of from about 300 nm to about 600 nm.

EXAMPLE 1

Preparation of colloidal selenium

To 200 ml of boiling distilled water, 2 ml of 3% SeO and 4.5 ml of freshly dissolved 1% ascorbic acid were added. The solution was refluxed for 10 minutes and cooled to room temperature. The resulting brownish red solution was then centrifuged for 20 minutes at 2500 g and 4° C. The pellet was resuspended in 200 ml of distilled water.

EXAMPLE 2

Conjugation of anti-$\beta$hCG polyclonal antibody with colloidal selenium

Polyclonal antibody against $\beta$hCG was adsorbed onto colloidal selenium by mixing 25 ul of goat anti-ghCG polyclonal antibody (4.6 mg/ml) in 2 ml of phosphate buffer (20 mM, pH 7.3) containing 30 mM NaCl with 25 ml of the above selenium colloid. After stirrinq for 10 minutes at 26° C, 1 ml of 1% polyethylene glycol (avg. MW 8000) was added. The solution was then centrifuged for 5 minutes at 5000 q and 4° C to obtain a dark red loose pellet. The pellet was resuspended in 1 ml of 0.1 g sodium phosphate buffer, pH 7.3, containing 0.15 g NaCl and 2% (w/v) BSA.

EXAMPLE 3

Assay of serum samples containing various amounts of hCGg

A. Spectrophotometric Analysis

In a series of test tubes were put 0.6 ml of 0.1 M sodium phosphate buffer, pH 7.3, containing 0.15 M NaCl and 30 ul of the above selenium-antibody conjuqate. To each tube, 70 ul of serum containing a specific amount of hCG standard were added. The tubes were briefly vortexed and incubated for 3 minutes at 26° C. before a spectrum was taken for each test tube on a spectrophotometer. Results of spectrophotometer measurements at $A_{356}$, $A_{420}$ and $A_{510}$ are shown in FIG.1. As seen in FIG. 1, the absorbance units associated with the hCG standards were essentially the same at various wavelengths, demonstrating the broad range at which the change of optical properties resulting from analyte/collidal non-metal labelled constituent can be monitored.

B. Radiative Energy Attenuation Analysis

Figure 2:
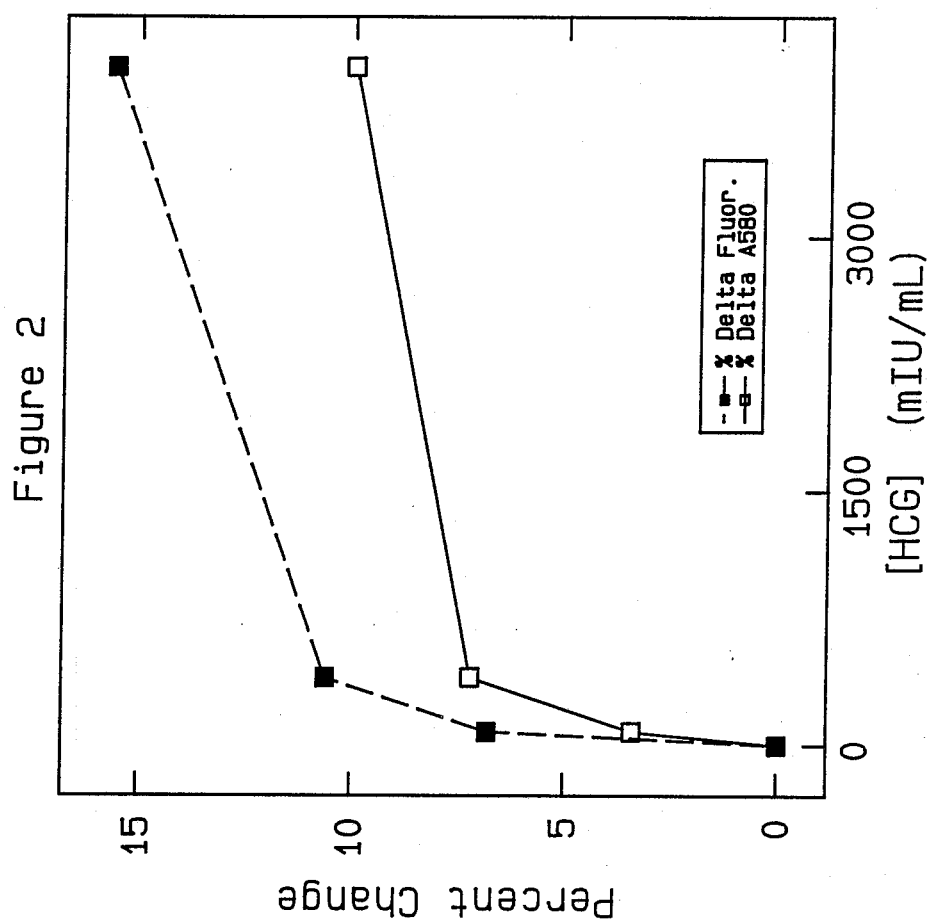
FIG. 2 is a graphic comparison of spectrophotometer and fluorescence intensity measurements of hCG using the method of the present invention.

In a separate experiment, g60 ul of the above conjugate of selenium and antibody were mixed with 1.2 ml of 0.1 g sodium phosphate buffer, pH 7.3, containing 0.15 M NaCl. To this solution 140 ul of serum sample containing various amount of hCG were added. Each solution was mixed and incubated at 26° C. for 3 minutes. To this solution 25 ul of fluorescein solution were added. The concentration of the fluorescein was to give 16,000 vertical intensity units on a Abbott TDx ® fluorometer when the 25 ul solution was mixed with 1.4 mL of the sodium phosphate buffer. The amount of fluorescence quenching due to the absorbance by selenium conjugate at the excitation and emission wavelengths of fluorescence (set at 485 and 525 nm on TDx®) was then measured employing a technique described in U.S. Pat. No. 4,495,293 (Radiative Energy Attenuation, REA, assay). The vertical intensity of fluorescence for each sample was collected. The fluorescence change due to the presence of different amounts of hCG in serum was then compared to the change in absorbance units measured by a spectrophotometer as described above and the results are shown in FIG. 2.

EXAMPLE 4

Solid phase immunoassay technique

A mix and run sandwich-type immunoassay device for the detection of swine antitrichina antibodies were produced. Nitrocellulose assay strips were prepared and were treated with trichina antigen immobilized at a detection zone.

Collidal selenium particles of Example I were utilized with various volumes (40, 80 and 150 ul aliquots) of concentrated selenium sol pipetted into individual vials containing 4 ml of water each and the pH of each, solution was adjusted to 7.2 by addition of 0.01 M potassium carbonate. To each of the vials was then added 150 ul of goat anti-swine antibody to IgG(H+L) (1 mg/ml concentration). The solutions were mixed and allowed to incubate for 10 minutes. A 0.5 ml aliquot of a 0.5% solution of alkaline treated casein was added to each solution and mixed well. Three ml aliquots of each selenium conjugate solution were centrifuged in 1 ml portions on a TDx ® table centrifuqe, and the pellets were combined for each conjugate after the supernatent was decanted off. The combined pellets of each conjugate were resuspended with a solution of 4% casein in 20 ul of TBS. 0.5 ul aliquots of the selenium particle labelled antibody solutions were then mixed with sera samples comprising varying concentrations of swine antitrichina antibodies.

The sample mixtures were contacted to the nitrocellulose strips, and specific binding of the labelled antibody was detected at the detection zone. All conjugates gave a visible red color which indicates a positive signal, with the conjuqate utilizing 80 nm selenium particles providing the best results. All the conjugate solutions were tested against a negative control which indicated no specific binding.

Although this invention has been described with respect to specific modifications, the details are not to be construed as limitations, for it will be apparent that various equivalents, changes and modifications may be resorted to without departing from the spirit and scope thereof and it is understood that such equivalent embodiments are intended to be included therein.

What is claimed is:

1. A method for determining the presence or amount of an analyte in a sample comprising the steps of: contacting said sample with a non-metal labelled constituent comprising colloidal non-metal inorganic particles selected from the group consisting of sulfur, selenium, and tellurium having conjugated thereto a binding component capable of specifically recognizing said analyte; and then determining the presence or amount of analyte/colloidal non-metal particle complexes as a measure of the amount of analyte in the sample.

2. The method of claim 1 wherein said colloidal non-metal particles are selenium particles.

3. The method of claim 1 wherein said binding component conjugated to said non-metal particles is selected from the class consisting of antigen, hapten and antibody.

4. The method of claim 3 wherein said binding component is an antibody.

5. The method of claim 1 wherein said colloidal non-metal particles have a particle size of from about 3 nm to 450 nm.

6. The method of claim 1 wherein said colloidal non-metal particles have a particle size of from about 11 nm to about 200 nm.

7. The method of claim wherein said antibody is adsorbed onto said colloidal non-metal particles.

8. The method of claim 1 wherein said sample is contacted with an aqueous dispersion from about 0.005% to 0.1% weight/volume of said colloidal non-metal particles.

9. The method of claim 1 wherein said sample is contacted with an aqueous dispersion having from about 0.02 to about 0.04 weight/volume of said colloidal non-metal particles.

10. The method of claim 1 wherein contacting said sample with said colloidal non-metal labelled constituent involves forming a reaction mixture of said sample and aqueous dispersion of colloidal particles so that said analyte and said colloidal particles agglutinate to form complexes of analyte/colloidal non-metal particles.

11. The method of claim 1 wherein said analyte/colloidal non-metal particle complexes are U analyzed by spectrophotometric means.

12. The method of claim 1 wherein said analyte/colloidal non-metal particle complexes are analyzed by fluorescence intensity measuring means.

13. A method for determining the presence or amount of an analyte in a sample comprising the steps of: forming a reaction mixture of said sample with a selenium labelled constituent comprising an aqueous dispersion of colloidal selenium particles having conjugated thereto a binding compound capable of recognizing said analyte; and determining the presence or amount of analyte/selenium labelled constituent agglutination complexes in said reaction mixture by determining the change in optical properties as a measure of the amount of analyte in the sample.

14. The method of claim 13 wherein said selenium labelled binding component is selected from the class consisting of selenium labelled antigen, hapten, and antibody.

15. The method of claim 14 wherein said selenium labelled binding component is an antibody.

16. The method of claim 13 wherein said colloidal selenium particles have a particle size of from about 3 nm to about 450 nm.

17. The method of claim 16 wherein said colloidal selenium particles have a particle size of from about 11 nm to about 200 nm.

18. The method of claim 15 wherein said antibody is adsorbed onto said colloidal selenium.

19. The method of claim 13 wherein said sample is contacted with an aqueous dispersion having from about 0.005% to about 0.1% weight/volume of said collodial selenium.

20. The method of claim 13 wherein said sample is contacted with an aqueous dispersion having from about 0.02% to about 0.04% weight/volume of said collodial selenium.

21. The method of claim 13 wherein said analyte/colloidal selenium complexes are analyzed by spectrophotometric means.

22. The method of claim 13 wherein said analyte/colloidal selenium complexes are analyzed by fluorescence intensity measuring means.

23. A composition useful in the determination of an analyte in a sample, comprising:
a colloidal non-metal, inorganic particle selected from the group consisting of sulfur, selenium, and tellunium, and
a binding component.

24. The composition of claim 23 wherein said binding component is selected from the group consisting of an antigen, a hapten and an antibody.

25. The composition of claim 23 wherein said colloidal non-metal particles have a particle size of from about 3 nm to about 450 nm.

26. The composition of claim 25 wherein said colloidal non-metal particles have a particle size of from about 11 nm to about 200 nm.

27. The composition of claim 23 wherein said composition is present in an aqueous dispersion from about 0.005 to about 0.1 percent by weight/volume.

28. The composition of claim 27 wherien said composition is present in an aqueous dispersion from about 0.02 to about 0.04 percent by weight/volume.

* * * * *

UNITED STATES PATENT AND TRADEMARK OFFICE
CERTIFICATE OF CORRECTION

PATENT NO.  : 4,954,452

DATED       : September 4, 1990

INVENTOR(S) : D. Yost, et al.

It is certified that error appears in the above-identified patent and that said Letters Patent is hereby corrected as shown below:

Column 7, line 29, after "claim" insert --1--.
Column 7, line 46, after "are" delete "U"
Column 8, line 2, "Agqlutination" should read --agglutination--.

Signed and Sealed this

Thirty-first Day of March, 1992

Attest:

HARRY F. MANBECK, JR.

Attesting Officer

Commissioner of Patents and Trademarks